United States Patent [19]

Riederer

[11] Patent Number: 4,641,095

[45] Date of Patent: Feb. 3, 1987

[54] DETERMINATION OF T1 RELAXATION TIMES USED IN AUTOMATED NUCLEAR MAGNETIC RESONANCE IMAGE SYNTHESIS

[75] Inventor: Stephen J. Riederer, Durham, N.C.

[73] Assignee: Duke University Medical Center, Durham, N.C.

[21] Appl. No.: 734,101

[22] Filed: May 15, 1985

[51] Int. Cl.[4] .................................. G01R 33/20
[52] U.S. Cl. ................................ 324/309; 324/300; 324/307
[58] Field of Search ............. 324/300, 307, 309, 312, 324/313, 314

[56] References Cited

U.S. PATENT DOCUMENTS

| | | | |
|---|---|---|---|
| 4,498,048 | 2/1985 | Lee et al. | 324/309 |
| 4,506,222 | 3/1985 | Edelstein | 324/311 |
| 4,549,139 | 10/1985 | MacFall | 324/309 |
| 4,573,015 | 2/1986 | Abe et al. | 324/309 |

Primary Examiner—Michael J. Tokar
Attorney, Agent, or Firm—Oblon, Fisher, Spivak, McClelland, & Maier

[57] ABSTRACT

A method for providing improved estimates of the spin-lattice relaxation time T1 of an image in a Nuclear Magnetic Resonance (NMR) technique on a human body is disclosed which utilizes the application of a multiple spin-echo pulse sequence technique at two different pulse repetition times TR1 and TR2. The signals for each of the different repetition times are measured by first setting the longitudinal magnetization to an initial value and then waiting the appropriate repetition time in order to provide the measured signal. The magnetization is "flipped" into the x-y plane and the relationship between the measured values for each of the repetition times is utilized to form an algorithm whereby the calculated ratio of the measured signals allows for an initial estimate of T1. The process also utilizes the plurality of spin-echos in the multiple spin-echo pulse sequence to appropriately measure, at each of the echo-times TE(i), the decaying value of the measured first and second magnetization signals which, in turn, provides further estimates of T1 which are then weight averaged.

8 Claims, 12 Drawing Figures

DETERMINATION OF T1 RELAXATION TIMES USED IN AUTOMATED NUCLEAR MAGNETIC RESONANCE IMAGE SYNTHESIS

BACKGROUND OF THE INVENTION

1. Field of the Invention

This invention relates to a method for providing for improved measurement and determination of one of the intrinsic properties of materials subjected to automated nuclear magnetic resonance spectroscopy and imaging. More particularly, this invention is addressed to an improved method of determining the spin lattice relaxation time T1 which is directly related to specific properties of a tissue under consideration.

2. Discussion of the Background

The phenomena of nuclear magnetic resonance (NMR) has been utilized in recent years to produce images of the interior portions of a body, particularly human bodies, for diagnostic and other purposes. Although primarily used for examination of the interior of a body or a body portion having a variety of relatively soft tissues, NMR techniques can also be utilized under other widely varying circumstances. NMR images are utilized to portray characteristics of tissues under inspection which cannot be readily obtained using radiographic techniques and other imaging techniques.

The fundamental description of basic NMR physics and imaging techniques is found in Kaufmann et al, Nuclear Magnetic Resonance Imaging in Medicine, IgakuShoin Medical Publishers, Incorporated, New York and Tokyo (1981). The important features of the NMR technique which are commonly used in previous methods will now be elaborated upon.

The body under examination is subjected to one magnetic field which is usually constant in magnitude and another field which lies along at least one different vector from the first magnetic field. The second magnetic field is usually time-varying with the exact characteristics of each of these fields being a function of choice between any one of several available imaging techniques. During NMR examinations, the characteristics of the field energy must be preselected. As an example, one of the techniques called a spin-echo imaging, utilizes a preselected repetition time $T_R$, which is defined as the time between successive applications of the same pulse sequence. Also preselected is the sampling delay time $\tau$ (TAU) which is often set equal to TE/2 where TE is the time at which a spin-echo is measured. The first and second fields are applied to the tissue being examined in accordance with selected times and the results are detected and stored with the levels of the storage signals being correlated with their physical positions and with these levels being represented by a matrix of numbers. The numbers of the matrix are then displayed as a matrix of points or pixels which have different light or dark levels and the composite of these pixels forms an image having various contrasting areas.

A physician utilizes the results of these contrasting areas within the image to observe and analyze a "slice" of the body of which the image was made from and, in a medical context, to thereby form a diagnosis. The degree of contrast between the various areas is a function of $T_R$ and $\tau$ values which are selected before the measurement is made. The degree of contrast is also a function of the intrinsic properties of the materials including the net magnetization $M_0$ (which is proportional to Proton density), and the relaxation times T1 and T2.

While one particular set of values for $T_R$ and $\tau$ will produce an image with excellent contrast between certain sets of materials, it must be noted that this contrast will probably be insufficient between other types of materials being used. As a result of this varying contrast which depends upon the materials being used, it is necessary to make numerous sets of measurements with various values for $T_R$ and $\tau$. The images which result from these measurements use these different values of $T_R$ and $\tau$ in order to adequately examine various tissues involved.

This time consuming process in which the patient is often subjected to discomfort and sometimes repeatedly subjected to the effects of strong directional magnetic fields has been alleviated in accordance with the method and apparatus disclosed in copending application Ser. No. 727,674 filed Apr. 26, 1985, of which the present inventor is a coinventor. Utilizing the method and the apparatus of the copending application an apparatus is disclosed which is capable of obtaining intrinsic parameters of the body materials under examination and forming synthetic images based on those intrinsic parameters in order to permit the synthesis of images formed on the basis of other selectable parameters. The technique of the copending application provides a method in which a minimal number of measurements can be made and in which the data derived from these measurements is used to form synthetic images which include tissue contrast of a type which have been produced by measurements made with selected parameters such as $T_R$ and $\tau$ values other than those which were actually used for the measurements.

Even with respect to the improved overall apparatus and method for obtaining intrinsic parameters of the above identified copending application, there still exists a problem with respect to the actual determination of the intrinsic parameters from physically measured values. These intrinsic parameters, and more specifically the relaxation time T1, are generally found by acquiring NMR signals for several different repetition times $T_R$ and applying them as a function of time. The value of the spin lattice relaxation time T1 is a measure of the curvature of the smooth curve which most closely matches the measured signals. Because of the statistical uncertainty in the measured signals, there is uncertainty in the computed value of T1. Generally, this can only be compensated for by taking measurements several times at the repetition times initially used or by taking measurements at additional repetition times. In both cases the total scanning time must be increased.

Additional background information and disclosure of devices and techniques in the field to which this invention relates can be found in the following articles and U.S. patents.

F. W. Wehrli, J. R. McFall, and G. H. Glover. The dependence of nuclear magnetic resonance (NMR) image contrast on intrinsic and operator-selectable parameters presented at the meeting of the SPIE, Medicine XII, volume 419, April 1983.

I. R. Young, et al. Contrast in NMR Imaging. Presented at the Society of Magnetic Resonance in Medicine, August 1983.

D. Ortendahl, et al Calculated NMR images. Presented at the Society of Magnetic Resonance in Medicine, August 1983.

P. L. Davis, et al. Optimal spin-echo images for liver lesions by retrospective calculations. Presented at the Society of Magnetic Residence in Medicine, August 1983.

| U.S. Pat. No. | Inventor |
| --- | --- |
| 3,789,832 | Damadian |
| 4,045,723 | Ernst |
| 4,284,948 | Young |
| 4,292,977 | Krause et al |
| 4,297,637 | Crookes et al |
| 4,307,343 | Likes |
| 4,318,043 | Crookes et al |
| 4,354,499 | Damadian |
| 4,355,282 | Young et al |
| 4,390,840 | Ganssen et al |

SUMMARY OF THE INVENTION

Accordingly, one object of the invention is to provide a novel method of determining the spin lattice relaxation time T1 by utilizing the multiple spin-echo technique in order to obtain the equivalent of several semi-independent measurements at each repetition time $T_R$ which subsequently improves the statistical precision and allows for the formation of improved estimates of the spin lattice relaxation time T1 without any additional scanning time.

It is another object of the invention to provide a method whereby the spin lattice relaxation time T1 is developed from the longitudinal magnetization Mz by altering the magnetization Mz away from its equilibrium position $M_0$. The initial value of $M_z$ is set to some known quantity such as 0 or $-M_0$ and, after a predetermined repetition time $T_R$ the initial value of $M_z$ is "flipped" into the transverse plane in order to detect a free induction decay (FID) signal. This process is repeated at least twice using different $T_R$ values which are then used to estimate T1 through the use of the "multiple spin-echo" technique.

It is another object of the present invention to provide a method whereby N spin-echo signals are measured at respective echo times TE(i), i.e., =1 ..., N for each of a multiple of different TR values. The first echo for each of the TR values is used to estimate a first value for T1, T1(1), with the second echoes being used to form another estimate, T1(2) etc. for all N sets of echoes and with a final estimate of T1 made using all of the estimates in a weighted average whereby the determination of T1 for a single material is generalized to the formation of a T1 image.

It is another object of the present invention to provide the improved determination of T1 by signal averaging of the multiple spin-echo measurements which are provided at each of TR1 and TR2 by image synthesis prior to performing the T1 fit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1A:
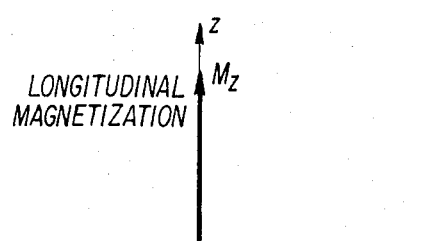
FIGS. 1A and 1B is a graphical representation of the longitudinal and transverse magnetization, respectively.
Figure 1B:
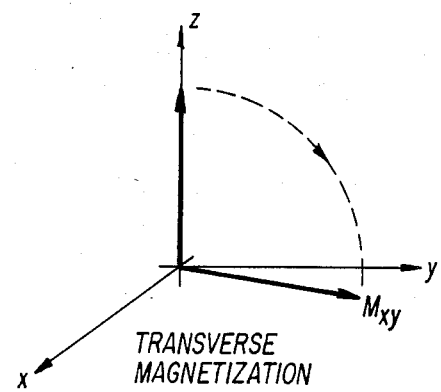

Referring now to the drawings, wherein like reference numerals designate identical or corresponding parts throughout the several views, and more particularly to FIG. 1A thereof, there is illustrated a graphical representation of the longitudinal magnetization parameter ($M_z$) which is aligned in the z axis of the xyz coordinate system. Because the quantity which is to be measured is the spin lattice relaxation time T1, which is defined as the recovery time of the longitudinal magnetization $M_z$ after it has been altered away from its equilibrium position $M_0$, this concept with respect to the longitudinal magnetization is a first step in developing a determination of T1. The FIG. 1B illustrates the "flipping" of the magnetization into a transverse plane (x-y). $M_z$, illustrated in FIG. 1, is never measured directly but is subjected to the flipping shown in FIG. 1B. The length of the "flipped" magnetization $M_{xy}$, immediately after the flip, equals that of $M_z$ prior to the flip. Because the measurement of T1 is actually the recovery time of the longitudinal magnetization after it has been altered away from an equilibrium position $M_0$, the process naturally involves the initial setting of the $M_z$ at a known quantity such as 0 or $-M_0$.

Figure 2A:
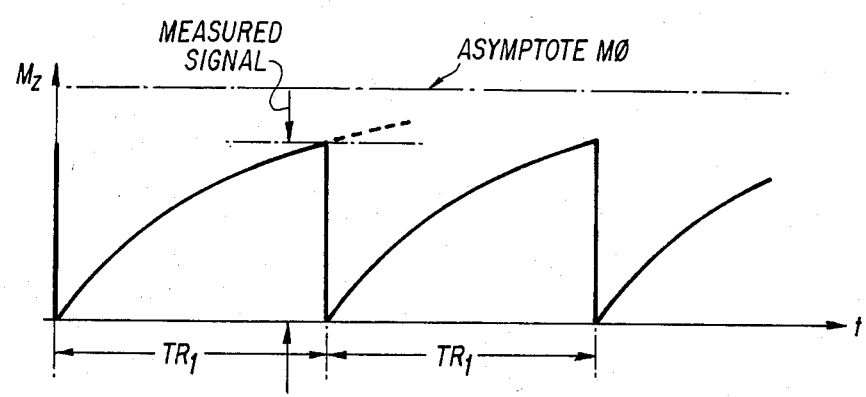
FIGS. 2A and 2B is a graphical representation of the behavior of the length of the longitudinal magnetization as a function of time at different repetition times $T_R$.
Figure 2B:
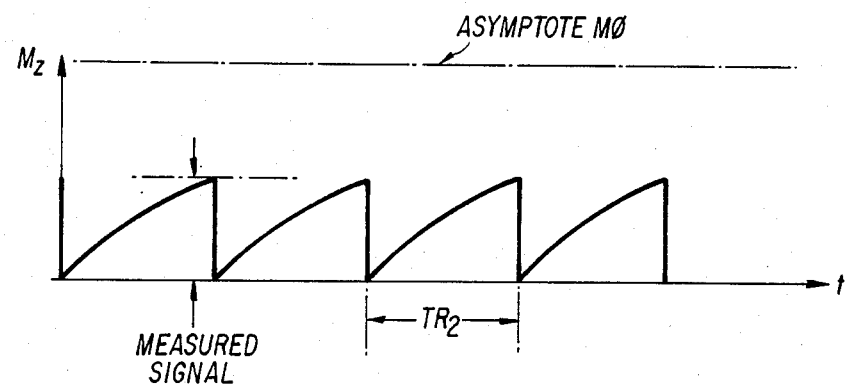

The FIG. 2A illustrates that the magnetization $M_z$ is initially set at a 0 value and then begins to change as a function of time toward an asymptote $M_0$. After some selected repetition time TR2 the signal is measured and the magnetization is returned to the starting initial value or 0 in the instance of FIG. 2A. The FIG. 2B illustrates a value of $TR_1$ which is less than $TR_2$ for purposes of providing a measured signal. It can be seen that the time period $TR_1$ is less than $TR_2$ so that the measured signal is less for a shorter time period or in another words the magnetization has not had as much opportunity to approach the asymptotic value as in the instance of FIG. 2A which has a longer value for TR.

Figure 3:
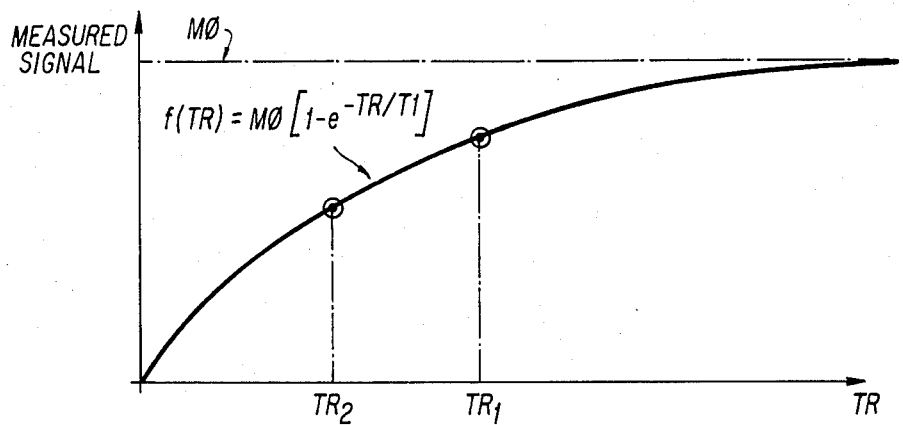
FIG. 3 illustrates a plotting of the measurements made from FIGS. 2A and 2B with respect to estimating T1 utilizing a characteristic equation.
Figure 7:
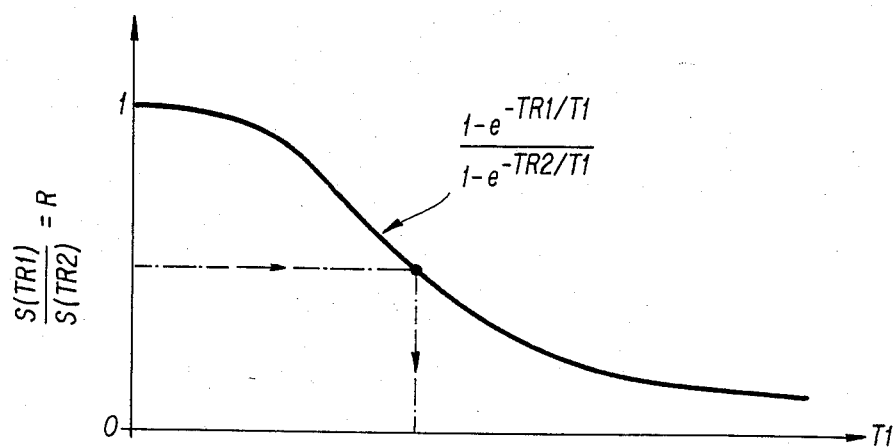
FIG. 7 is a graphical representation of the actual determination of T1 for measurements at two TR times.

The FIG. 3 illustrates how the measurements made from FIGS. 2A and 2B are plotted and that these values fit along a curve defined by the equation such that the measured signal is a function of the asymptote and TR as well as T1. More specifically, $S(TR) = M_0[1 - \exp(-TR/T1)]$ from the measured signals as reflected by FIG. 3 and the known values which are utilized for $TR_1$ and $TR_2$ a first estimate can be made with respect to T1. The actual determination from the measurements of two different TR times is shown in FIG. 7 wherein the equation S(TR) for each of two different values TR1 and TR2 are divided in order to form a ratio R wherein $R = S(TR1)/S(TR2) = M_0[1 - \exp(-TR1/T1/T1]/M_0(1 - \exp(-TR2/T1)$ wherein R is the ratio of the two measurements for TR1 and TR2. The ratio of the expressions on the right side of the equation are a function of TR1 and TR2 (known quantities) and T1 (the desired unknown). FIG. 7 shows a plot of this ratio and from the knowledge of the value of R, i.e., from a knowledge of the values of the measured signals, the FIG. 7 yields a value for T1, as shown.

As previously indicated, the calculation described above with respect to forming a computed value of T1 has inherent statistical uncertainty in the measured signals which are utilized. Previously, the only way known to compensate for this statistical uncertainty was to take measurements several times at each of the repetition values or by taking measurements at additional repetition times. In both instance, the total scanning time must be increased. In order to overcome this problem additional measurements are obtained by utilizing a multiple a spin-echo treatment.

Figure 4A:
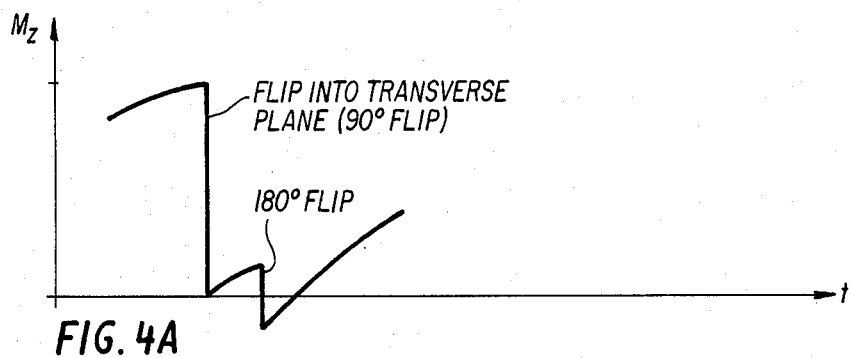
FIGS. 4A and 4B detail the measurement process for a conventional single spin-echo.
Figure 4B:
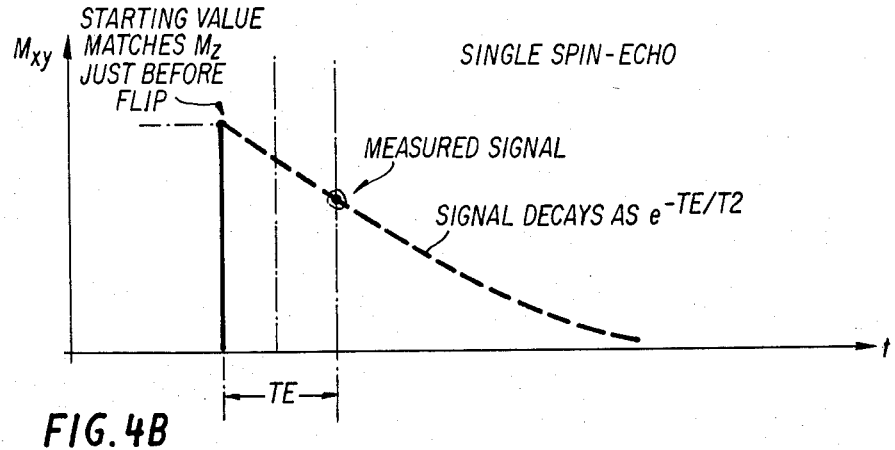

A single spin-echo treatment is shown in FIG. 4A which involves a flipping of the longitudinal magnetization into the transverse plane in a manner similar to the showings of FIGS. 1A and 1B. This is a 90° flip and the starting value, as shown in FIG. 4B, in the x-y plane for the magnetization $M_{xy}$ is equal to the longitudinal magnetization $M_z$ just prior to the flip. At a time period TE/2 a 180° flip occurs which basically involves going from a plus value to an equivalent negative value, ergo 180°. When the signal after the 180° flip recovers to the zero point or in another words after a value of TE from the initial 90° flip, a measured signal is obtained as shown in FIG. 4B. The decay of the signal value from the starting value through the measured value at time TE is controlled by the exponential function EXP $(-TE/T2)$. The value T2 is a known value which is defined as the spin-spin relaxation time and which is determined by well known methods.

A brief discussion of a prior art determination of T2 will now be given. The NMR signals are measured for fixed repetition time TR and several echo times $TE_i$, $i=1, 2, \ldots, N$. The known methods involve the use of regression techniques using a curve of the form: P exp $(-TE/T2)$ wherein P is defined as the pseudo-density which is the extrapolation of the measured signals back to a TE of zero where P and T2 are adjusted so that the curve most closely matches the measured signals. This is usually done in one of two ways. Either the squared deviations of the original signals are minimized in which case $X_1{}^2 = \Sigma[S_i - P \exp[-TEi/T2)]]^2$ or in another fashion and more commonly logarithms are first taken and minimizing the value $X_2{}^2 = \sigma[\text{Ln}S_i - [\text{ln}P - (TEi/T2)]]^2$.

As is further well known to those skilled in the art of regression methods, the partial derivatives $\delta x_2{}^2/\delta (\text{ln}P)$ and $\delta X_2{}^2/\delta (1/T2)$ are formed and then set equal to 0. Then the resulting 2×2 linear system is solved for lnP and 1/T2. Upon taking the reciprocal of 1/T2 the specific value of T2 is determined which is most consistent with the measured signals $S_i$. This process is then done for every pixel in the image in order to determine the various T2 value.

The curve defined by P exp $(-TE/T2)$ wherein P is defined as the pseudo-density which is the extrapolation of the measured signals back to a TE value of 0, can be utilized to produce a synthesis of an image at each TR value (TR1 and TR2) at some echo-time TE other than 0. These synthetic images are then inserted into the T1 fit, to be described later as part of the present invention. The motivation for using the synthesizing of an image is that at each TR any synthetic image formed is a "average" of the N spin-echo measurements made there.

For each TR, the P represents the extrapolation along the TE direction of the original spin-echo signals to an echo-time of 0. The synthesized image, referred to above, provides a further generalization by actually calculating or synthesizing signals at some arbitrary nonzero value of TE using the P and T2 values resulting from the regression:

$$S_{SYN}(TR1, TE) = P(TR1) \exp(-TE/T2)$$

$$S_{SYN}(TR2, TE) = P(TR2) \exp(-TE/T2)$$

Because the synthesized signals are formed for the same TE they can be inserted into the T1 fit to be described later in order to yield the estimate $\overline{T1}$ (SYN). In particular, the echo-time TE used for the above two equations can be chosen which maximizes the signal-to-noise ratio in the synthetic signals for the given TR's, thereby optimizing the precision in the subsequent T1 fit. Both the T1 "fit" and the maximizing of the signal-to-noise ratio is described hereinafter.

Figure 5A:
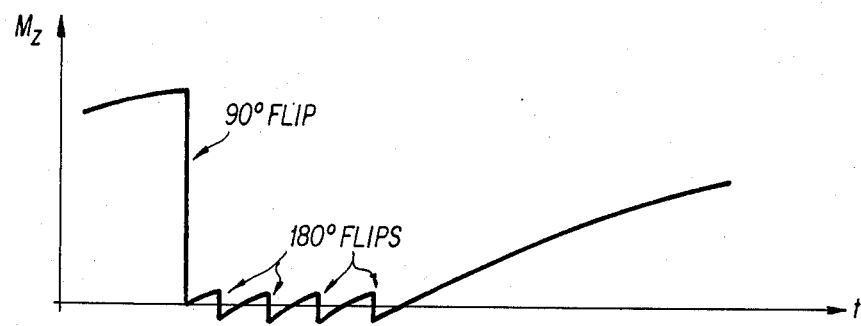
FIGS. 5A and 5B show the instance of a multiple spin-echo analogous to the FIG. 4 measurement.
Figure 5B:
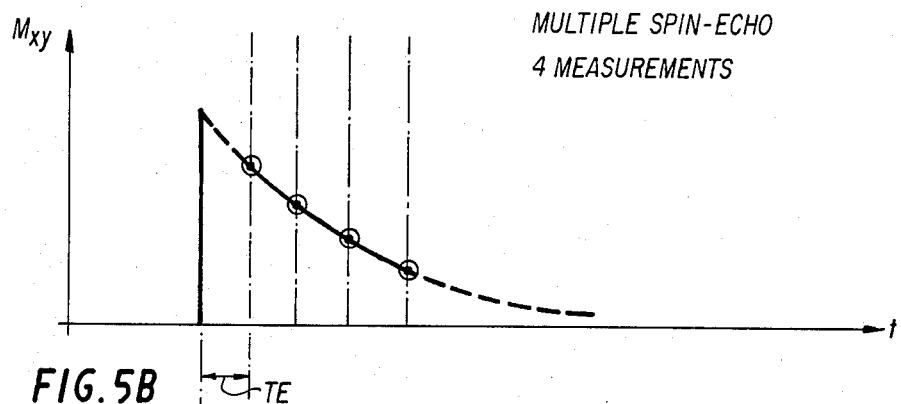

Referring now back to the drawings and more specifically to FIGS. 5A and 5B, there is shown a graphic illustration of the application of the multiple spin-echo technique which provides for the essence of the improved method by utilizing for a single scanning time the various measured signals (4 in the instance of FIG. 5) which are used to provide the various estimates for T1 at each of the four TE times of the multiple spin-echo technique. This provides for an increased number of measurements of T1 without an increased number of scans. Thus, the multiple spin-echo technique allows for the equivalent of several semi-independent measurements at each TR. With this increased number of measurements the net statistical precision which will be discussed below is improved and superior estimates of T1 can be had with no additional scanning time.

Figure 6:
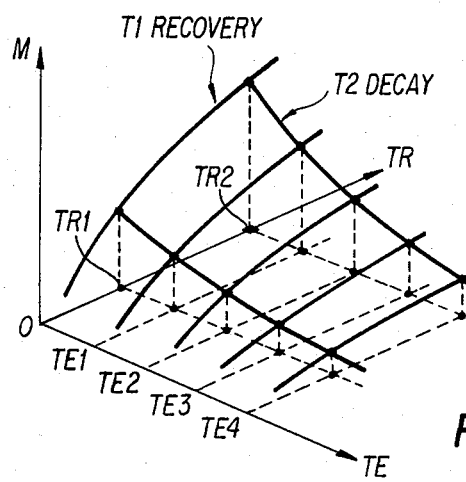
FIG. 6 is a three-dimensional plot of the magnetization of an arbitrary material which is measured in a spin-echo treatment as a function of the repetition time $T_R$ and the echo times TE.

The FIG. 6 illustrates a three-dimensional graph which shows the relationship between the longitudinal magnetization M, the repetition times TR and the spin-echo times TE. Essentially, FIG. 6 can be seen as an imposition of FIG. 3 onto FIG. 5B. It is important to note that, although the prior art methods of calculation of T2 have been discussed, such measurement is not essential with respect to the calculation of T1 because as seen from FIG. 7, for a single estimate of T1, the T2 is not a necessary function and is not a required quantity for the determination of T1.

The information contained in FIG. 5B and in FIG. 6 will now be used to provide an example of the determination of T1 based upon several values T1(i) where i=1, 2, 3 and 4 for the four measurements illustrated.

The technique involves the fitting of the spin-echo measurements at a first TE time of TE1 equal for example to 25 milliseconds for each of repetition times TR of, for example, TR1 equal to 500 and TR2 equal to 2,000 msec. The sequence of fittings is repeated for each of TE2, TE3 and TE4, which are subsequently formed at for example 50, 75 and 100 milliseconds.

When a four spin-echo treatment is utilized, the relative noise $\sigma$ in the computed P (Pseudo-density) is calculated to be at least 1.23 times higher than that in direct measurement using computational techniques known to those skilled in the art. The noise factor $\sigma$ is equal to the inverse of the relative signal to noise ratio (SNR) as $\sigma = 1/SNR$. Previous methods involved in the determination of T1 use the PD images resulting from 4-echo fits at several different TR values for obtaining a T1 fit or only used single spin-echo acquisitions. The present method involves using the spin-echos themselves at TE1, TE2, TE3 and TE4 and taking the average or weighted average of 4 fits. After the fits of the spin-echo measurement utilizing the graph of FIG. 7 are determined to fit the curve T1 at a spin-echo time of 25 milliseconds, 50 milliseconds, 75 milliseconds and 100 milliseconds, the four results are averaged and more specifically are weight averaged. This is accomplished using the following assumptions for purposes of illustrating an example utilizing the preferred embodiment.

For TE values of 25, 50, 75 and 100 milliseconds and for a T2 value of 100 milliseconds $\sigma$ is equal to the noise of the spin-echo image which for purposes of illustration is assumed to be one. The relative signal intensities exp $(-TE/T2)$ are:

| TE | Signal Intensity |
|---|---|
| 0 | 1 |
| 25 | .779 |
| 50 | .607 |
| 75 | .472 |
| 100 | .368 |

In the previous multi-echo techniques only the TE=0 point was utilized and in that instance the noise in the is $1.23 \times \sigma = 1.23$ so that the relative SNR in the T1 fit was $1/1.23 = 0.813$.

In the present technique the relative SNR for the 25 millisecond echo equals 0.779 for the particular value of T2 equal to the assumed 100 millisecond. Thus, it can be stated that the noise in each T1 fit for each echo is proportional to 1/signal, i.e., for TE=25 milliseconds then $T1 \pm \sigma/0.779$ (1.28), for TE2 of 50 milliseconds then $T1 \pm \sigma/0.607$ (1.65), for TE3=75 milliseconds then $T1 \pm \sigma/0.472$ (2.12) and for TE4= to 100 milliseconds then $T1 \pm \sigma/0.368$ (2.71).

In a first instance, if it is supposed that the estimates for T1 from each echo are combined in a simple average then,:

$T1_{ave} = \alpha_1 T1_{25} + \ldots + \alpha_4 T1_{100}$ with $\alpha_i = \frac{1}{4}$.

Thus, the noise level would be given by:

$\sigma^2 = 1/16[(1.28)^2 + (1.65)^2 (2.12)^2 + (2.71)^2]$ $\sigma^2 = 16.199/16 = 1.012$ $\sigma = 1.$ In a preferred embodiment the estimates are weighted to provide optimal combined estimates by weighted averages according to $\alpha_i$ is proportional to $1/\sigma_i^2$.

This leads to $\alpha_1\ 1/(1.28)^2 = 0.617$, $\alpha_2\ 1/(1.65)^2 = 0.367$, $\alpha_3\ 1/(2.12)^2 = 0.222$ and $\alpha_4\ 1/(2.71)^2 = 0.136$. The totality of the $\alpha_1, \alpha_2, \alpha_3$ and $\alpha_4 = 1.335$ In order to provide accurate signals these $\alpha$ values are normalized i.e., $\Sigma\alpha_i = 1$ so that $\alpha_1 = 0.456$, $\alpha_2 = 2.74$, $\alpha_3 = 0.166$ and $\alpha_4 = 0.102.$ In other words the sum of each of these values is approximately 1.

Utilizing these calculated values for $\alpha$ and the previously determined values for $\sigma_i$ than overall values for $\sigma^2 = \Sigma a_i^2 \sigma_i^2$ $= (.456)^2 (1.28)^2 + (.274)^2 (1.65)^2 + (.166)^2 (2.12)^2 +$ $(.102)^2 (2.71)^2 = .743$ and thus $\sigma = 0.861$ which is seen to be a 42% improvement over the $\sigma = 1.28$ which was the value with only a single measurement as far as a value measured at TE of 25 seconds without the further value estimates. This also represented a comparable improvement over the use of the pseudo-density images P in which case $\sigma$ is never less than 1.23. Thus this approximately 42% improvement has been gained while utilizing a single scan but with four measurements being taken due to the relationship established between the calculations concerning a multiple spin-echo technique and the subsequent T1 estimates obtained at the various spin-echo times TE(i).

The previously discussed synthetic images generated for values of TE other than zero for each of the TR values is a "average" of the N spin-echo measurements and thus the synthetic image has a superior SNR to that in any one of the original images. That is, the synthetic image having the highest possible SNR can then be used. In a mathematical context, the synthetic image having the highest possible SNR occurs when the synthesis is done at an echo-time TE which is substantially given by the equation $$TE = \frac{\sum_{i=1}^{N} TEi\ \exp[-2 \cdot TEi/T2]}{\sum_{i=1}^{N} \exp[-2 \cdot TEi/T2]}$$

The resultant noise in the T1 image made from these optimum synthetic images is identical in magnitude to that resulting from the weighted average case hereinbefore discussed.

Figure 8:
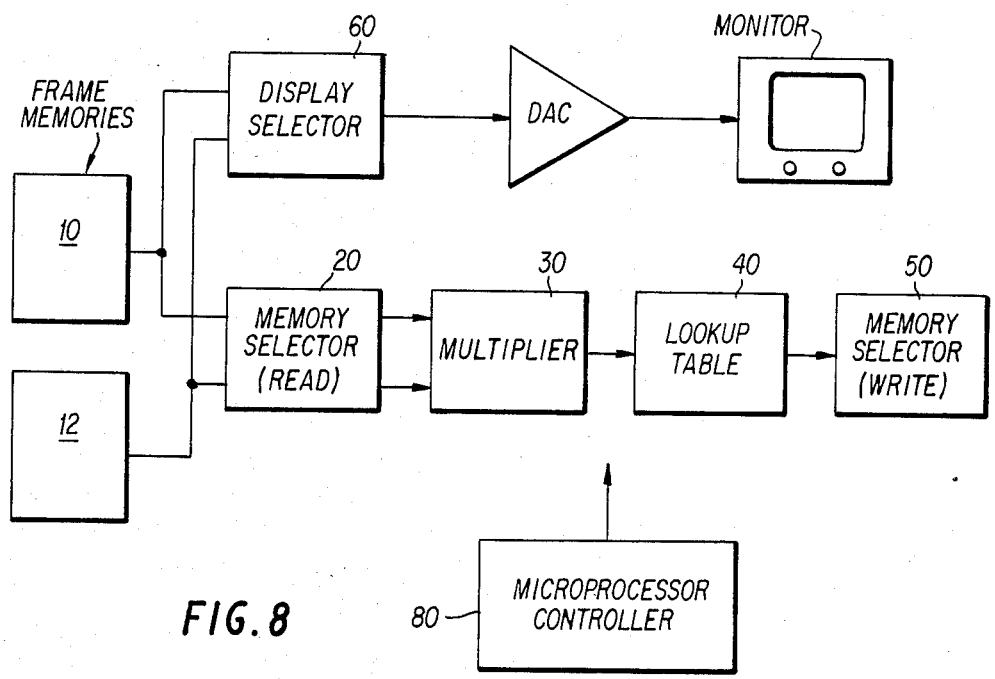
FIG. 8 is a block diagram of an image synthesis apparatus utilized to effect the method of the invention.

The aforementioned method for providing improved accuracy in the determination of T1, using but a single multiple spin-echo scan can be accomplished by the apparatus shown in FIG. 8, although those skilled in the art would recognize that other image synthesis apparatus configurations would be capable of carrying out the aforementioned improved method.

For purposes of simplification only two frame memories 10 and 12 have been utilized. In more detailed explanation with respect to the hardware of FIG. 8 and the accompanying multiple frame memory structure in accordance with an overall synthesis apparatus is disclosed in copending application Ser. No. 727,674, filed Apr. 26, 1985, of which the Applicant is a co-inventor.

The microprocessor controller 80 provides the overall control of the digital video processor units 20, 30, 40, 50 and 60. As previously indicated, the solving of the equation concerning a multiple spin-echo imaging technique would require more than the frame memories 10 and 12, and in fact would contain a total of 6 frame memories with 3 of the memories, not shown, ultimately containing the intrinsic parameters T1, T2 and $M_0$ after having been calculated in the aforementioned manner.

The output of each of the frames, illustrated as 10 and 12 is fed to the digital video processor which consists of the processor selector 20, the multiplier 30, the look-up table (LUT) 40 and the memory selector/wright 50. When the FIG. 8 construction is utilized to calculate the spin-echo equations, an arithmatic logic unit (ALU) (not shown) is further utilized in conjunction with the output of the multiplier and the memory selector. The microprocessor 80 dictates that when a multiplication operation is to be performed the not shown arithmatic logic unit simply receives the output from the memory selection 20 and when a exponential factor is to be generator, this is performed directly by the LUT 40. If on the other hand, the term which is being calculated with respect to the spin-echo equation does not use an exponential factor the microprocessor only directs the LUT 40 to pass through the operation to the memory/write enable which in turn outputs on a specific line the calculated value to particular ones of the frame memories. This will become more clear when taken in conjunction with the following description of a sequence of activities to generate the value T1 which provides the improved determination according to the aforementioned and described method.

During a first time period the signals measured for every pixel for each of two TR (repetition times) is stored in the individual frame memories 10 and 12 as the function S(TR1) and S(TR2), respectively. The reciprocal of S(TR2) is obtained by passing the value of frame memory 12 through the high speed look up table 40 and during the same frame interval the reciprocal image obtained in look up table 40 is stored back into frame memory 12.

In the next step the product of frame memories 10 and 12 i.e., S(TR1)×1/S(TR2), is utilized to obtain the "ratio" image $R=S(TR1)/S(TR2)$. This is accomplished through the use of the high speed multiplier 30 and the result of this multiplication is sent back to frame 12.

In the final step the ratio image R is read out from the frame 12 and passed through the LUT 40 which is now loaded with the transfer function previously discussed and shown in FIG. 7. More specifically the transfer function which is loaded into the look up table 40 is given by the equation $[1-\exp(-TR1/T1)]/[1-\exp(-TR2/T1)]$. Thus for a value of R stored in the frame memory 12, the look up table 40, programmed with the above algorithm by the microprocessor 80 provides an output T1 which is fed back and stored in the frame memory 12.

The remainder of the calculations with respect to the multiple spin-echo measurements at various spin-echo times TE can be easily calculated in the manner explained previously with respect to providing multiple measurements for other values of T1 which are used in the overall weighted average. That is, once the several measurements on the single scan are accomplished for each echo time TE, the estimates for T1 can be properly averaged at each TE in order to improve the precision, as detailed previously. These techniques can be implemented using the above computer hardware or primarily computer software.

Thus, the invention which has been described provides for an improved method of determining the T1 relaxation time which can be accomplished with improved accuracy, and a reduced scanning time because of the multiple spin-echo technique which is applied to the determination using the weighted average technique described above. Obviously, numerous additional modifications and variations of the present invention, such as the use of more than two repetition times and the subsequent change in algorithms necessary to change the T1 estimate at each echo-time or alternate ways of performing the T1 fit, are possible in light of the above teachings. It is therefore to be understood that within the scope of the appended claims, the invention may be practiced otherwise than as specifically described herein.

What is claimed as new and desired to be secured by Letters Patent of the United States is:

1. A method for determining the spin-lattice relaxation time T1 of an image during a Nuclear Magnetic Resonance (NMR) measurement technique on a human body comprising the steps of:

subjecting said body to magnetic fields in accordance with a NMR technique using a multiple spin-echo pulse sequence at two different predetermined stored pulse repetition times TR1 and TR2;

measuring a first signal S(TR1) at a first one of (TR1) of said two repetition times including the steps of setting a longitudinal magnetization to an initial predetermined value $M_0$, waiting a first period of time equal to a first pulse repetition time TR1, and then flipping the longitudinal magnetization Mz by 90° into the x-y plane wherein the value of x-y plane magnetization immediately after the step of flipping is said first signal, called the transverse magnetization, which is equal to the value of the longitudinal magnetization immediately prior to the step of flipping and wherein said first signal S(TR1) is expressed by a first equation $S(TR1)=M_0[1-\exp(-TR1/T1)]$ where $M_0$ is a constant;

measuring a second signal at a second one TR2 of said two repetition times including the step of setting a longitudinal magnetization to an initial predetermined value $M_0$, waiting a second period of time equal to said second pulse repetition time TR2, and then flipping the longitudinal magnetization by 90° into the x-y plane, wherein the value of the x-y plane magnetization immediately after the step of flipping is said second signal, called the transverse magnetization, which is equal to the value of the longitudinal magnetization immediately prior to the step of flipping and wherein said measured second signal S(TR2) is expressed by a second equation $S(TR2)=M_0[1-\exp(TR1/T1)]$;

storing the value of said measured first and second signals;

allowing said first and second measured signals to decay away at a characteristic time T2 and measuring said decaying signal at a plurality of echo times TE(i) i=1, ..., N wherein said echo times are associated with 180° flips each associated with one of a multiple of spin-echos in said multiple spin-echo pulse sequence;

storing said measured decaying signal values at each of said echo times TE(i) for each of said first and second pulse repetition times TR1, TR2;

forming a first ratio R of said first to said second measured values;

solving a third equation $R=[1-\exp(TR1/T1)]/[1-\exp(-TR2/T1)]$ for an initial T1 value by using the stored values of said first ratio R and said pulse repetition times TR1 and TR2;

forming a plurality of secondary ratios $R_1 ..., R_N$ of said measured decaying signal values at each of said echo times TE(i) i=1 ..., N for said first repetition time to said measured decaying signal values at each of said echo times TE(i) i=1 ..., N for said second repetition time, respectively;

solving said third equation for a plurality of T1(i) i = 1 ..., N values using said plurality of secondary ratios $R_1 ... R_N$; and finding the average value of at least said plurality of T1(i) i = 1 ..., N values.

2. A method according to claim 1, wherein the step of finding the average value involves taking a weighted average $$T1 = \sum_{i=1}^{N} a(i) T1(i)$$

where a(i) are predetermined constants.

3. The method according to claim 2, wherein a(i) are proportional to exp (−2 TE(i)/T2) where T2 is said characteristic time and is defined as a spin-spin relaxation time.

4. The method according to claim 1, wherein said step of finding the average value includes the average value of said plurality of T1(i) values and said initial T1 value.

5. The method according to claim 1, wherein N=4 and TE(1)=25 msec, TE(2)=50 msec, TE(3)=75 msec and TE(4)=100 msec.

6. The method according to claim 1, wherein said first repetition time TR1 is less than said second repetition time TR2.

7. A method for determining the spin-lattice relaxation time T1 of an image during a Nuclear Magnetic Resonance (NMR) measurement technique on a human body comprising the steps of:

subjecting said body to magnetic fields in accordance with a NMR technique using a multiple spin-echo pulse sequence at two different predetermined stored pulse repetition times TR1 and TR2;

measuring a first signal S(TR1) at a first one of (TR1) of said two repetition times including the steps of setting a longitudinal magnetization to an initial predetermined value $M_0$, waiting a first period of time equal to a first pulse repetition time TR1, and then flipping the longitudinal magnetization Mz by 90° into the x-y plane wherein the value of x-y plane magnetization immediately after the step of flipping is said first signal, called the transverse magnetization, which is equal to the value of the longitudinal magnetization immediately prior to the step of flipping and wherein said first signal S(TR1) is expressed by a first equation $S(TR1) = M_0[1 - \exp(-TR1/T1)]$ where $M_0$ is a constant;

measuring a second signal at a second one TR2 of said two repetition times including the step of setting a longitudinal magnetization to an initial predetermined value $M_0$, waiting a second period of time equal to said second pulse repetition time TR2, and then flipping the longitudinal magnetization by 90° into the x-y plane, wherein the value of the x-y plane magnetization immediately after the step of flipping is said second signal, called the transverse magnetization, which is equal to the value of the longitudinal magnetization immediately prior to the step of flipping and wherein said measured second signal S(TR2) is expressed by a second equation $S(TR2) = M_0[1 - \exp(TR1/T1)]$;

storing the value of said measured first and second signals;

allowing said first and second measured signals to decay away at a characteristic time T2 and measuring said decaying signal at a plurality of echo times TE(i) i = 1, ..., N wherein said echo times are associated with 180° flips each associated with one of a multiple of spin-echos in said multiple spin-echo pulse sequence;

storing said measured decaying signal values at each of said echo times TE(i) for each of said first and second pulse repetition times TR1, TR2;

subjecting at each of said two different predetermined stored pulse repetition times TR1 and TR2 said measured decaying signal values at each of said echo-time to a regression which provides estimates of pseudo-density (P) and the spin-spin relaxation time (T2);

calculating a synthetic spin-echo P exp (−TE/T2) where TE is an arbitrary operator specified value for each of TR1 and TR2;

forming a ratio of said synthetic spin-echo of said first repetition time to said synthetic spin-echo of said second repetition time;

solving a third equation $R = [1 - \exp(TR1/T1)]/[1 - \exp(-TR2/T1)]$ for a T1 value by using the values of said first ratio R and said pulse repetition times TR1 and TR2.

8. The method according to claim 7 wherein the value of TE is substantially given by the equation $$TE = \frac{\sum_{i=1}^{N} TEi \exp[-2 \cdot TEi/T2]}{\sum_{i=1}^{N} \exp[-2 \cdot TEi/T2]}$$

* * * * *